United States Patent
Lamade et al.

(10) Patent No.: US 6,266,548 B1
(45) Date of Patent: *Jul. 24, 2001

(54) INDOTRACHEAL TUBE

(76) Inventors: Wolfram Lamade; Uta Meyding-Lamade, both of Sitzbuchweg 97, D-69118 Heidelberg (DE)

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/102,516

(22) Filed: Jun. 22, 1998

(30) Foreign Application Priority Data

| Dec. 22, 1995 | (DE) | 295 20 326 U |
| Mar. 6, 1996 | (DE) | 296 05 130 U |
| Dec. 12, 1996 | (WO) | PCT/EP96/05504 |

(51) Int. Cl.$^7$ ............................ A61B 5/0402
(52) U.S. Cl. ............................ 600/375; 600/393
(58) Field of Search ............... 600/433, 434, 600/561, 585, 593, 375, 393

(56) References Cited

U.S. PATENT DOCUMENTS 4,351,330 * 9/1982 Scarberry .
5,024,228 * 6/1991 Goldstone et al. .
5,025,786 * 6/1991 Siegel .
5,056,532 * 10/1991 Hull et al. .
5,505,700 * 4/1996 Leone et al. .

FOREIGN PATENT DOCUMENTS

| 8915538 | 10/1990 | (DE) . |
| 0438863 | 11/1990 | (EP) . |
| 2294642 | 11/1995 | (GB) . |
| 7908514 | 11/1979 | (NL) . |

OTHER PUBLICATIONS

Head and Neck Plastic Surgery, Fabrication of a Custom ElecTrode Endotrachael Tube, Joel A. Sercarz MD; Gerald S. Berke, MD; James Rothschiller; Ye Ming, MD; Sep. 1991; pp. 1024 &1025.

* cited by examiner

Primary Examiner—John P. Lacyk
Assistant Examiner—Pamela L. Wingood
(74) Attorney, Agent, or Firm—Helfgott & Karas

(57) ABSTRACT

A double balloon endrotrachael tube has a hose section (1) and at least two adjacent balloons (3; 6) that may be independently inflated. Atraumatic sensors for monitoring the motor larynx nerves are associates to the upper balloon (3). For that purpose, electric and/or electromagnetic sensors (4) are arranged on the surface of said balloon.

6 Claims, 6 Drawing Sheets

INDOTRACHEAL TUBE

Figure 2:
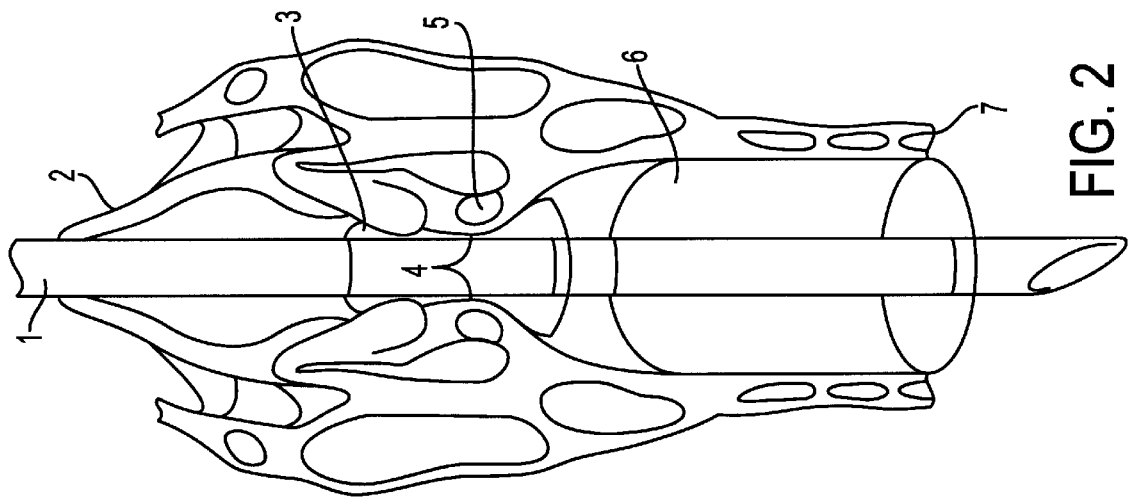

The present invention relates to a double-balloon endotracheal tube, comprising a tube segment and at least two balloons which are arranged adjacent to one another and can be expanded independent of one another, of which the top one has atraumatic sensors for checking the motor laryngeal nerves assigned to it.

Damage to the recurrent laryngeal nerve (nervus laryngeus recurrens=NLR) is a serious complication in throat operations. Loss of function on both sides is a life-threatening emergency situation. Large numbers of statistics for over 12,000 struma resections showed a recurrent laryngeal nerve paresis rate of 1.2% and 5.2%, respectively, regardless of whether or not the nerve was presented (exposed) during the operation. Therefore there is essentially unanimity concerning the fact that the NLR should be exposed during thyroid operations, in order to preclude accidental injury. A variant course and the extremely small size of its structure frequently result in difficulties in identification of the nerve. This is particularly true with regard to large strumae, repeat operations, and tumor operations. Here the rate of injury of the NLR is as high as 20%. Damage to the superior laryngeal nerve (nervus laryngeus superior= NLS) is reported for up to 25% of all patients, even if the strumae are uncomplicated. In the majority of cases of postoperative function problems of the NLR, the surgeon is able to definitely preclude the possibility that the nerve has been cut through. Therefore the cause of the damage is primarily due to stretching or compression of the nerve, or its being knotted into the surgical suture. This results in the urgent need for continuous, intraoperative monitoring of the NLR, in order to recognize the threat of injury to the nerve during mobilization of the thyroid, in timely manner.

Many different attempts at intraoperative identification of the NLR and intraoperative monitoring of its function have already been undertaken. For example, Dale B. Smith and others, in the essay "A device for the intraoperative identification of the recurrent laryngeal nerve in piglets" (Otolaryngology—Head and Neck Surgery 1989, 100, p. 137–145), describe the double-balloon endotracheal tube mentioned initially. Here, the sensors assigned to the top balloon function hydraulically. The corresponding tube is introduced into the trachea to such an extent that the top balloon comes to rest in the region of the glottis. In this position, the tube is fixed in place in the trachea and sealed with regard to the latter, in that the bottom balloon is pumped up. Subsequently, the top balloon is expanded until it rests against the vocal cords. The NLR is electrically stimulated during the operation, which results in a corresponding muscle contraction of the glottis, with the prerequisite that the NLR is not damaged. This muscle contraction results in a pressure increase in the top balloon, which is indicated on the pressure gauge to which the latter is connected.

The decisive disadvantage of this known endotracheal tube is that using this tube, it is only possible to detect significant injury of the NLR which has already occurred, as demonstrated by gross changes in its function. However, impairment of individual axons of the nerve, which is attributable to external influences, cannot be detected. Likewise, slight and reversible traumas of the NLR, such as traction on the nerve and therefore the threat of damage that has not yet occurred, cannot be shown with the known endotracheal tube.

Since the NLR serves not only to close but also to open the vocal cords, traumas can remain undiscovered or even be incorrectly interpreted, if they do not result in a pressure increase but in constant pressure or even a pressure decrease.

The process cannot be used to detect the electrical inherent activities of the nerves which are triggered by mechanical contact and appear as so-called "spikes" in the EMG. Their duration is too short to be detected and quantified by the rough method of measuring pressure. Fundamentally, therefore, pressure measurement in the glottis does not solve the task to be solved, that of reliable intraoperative monitoring of the tracheal nerves.

Furthermore, various other methods and corresponding devices were described, which were intended for intraoperative presentation of the electrically stimulated NLR. D. J. Premachandra and others, in their essay "Intraoperative identification of the recurrent laryngeal nerve and demonstration of its function" (Laryngoscope 1990, 100, p. 95–96) describe the visualization of vocal cord mobility by means of a rigid endoscope. A. G. James and others, in their essay "A simple method for identifying and testing the recurrent laryngeal nerve" (Surgery Gynecology Obstetrics 1985, 161; p. 185–186), explained that the integrity of the NLR can be tested by palpation of the m. cricothyroideus. J. G. Spahn and others, in their essay "Identification of the motor laryngeal nerves—a new electrical stimulation technique" (Laryngoscope 1991, 91; p. 865–868), described that a fine needle placed in the fissure of the glottis performs visible movements during a movement of the glottis triggered by electrical stimulation of the NLR. A traumatic derivation process by means of a bipolar needle electrode was described by W. E. Davis in his essay "Recurrent laryngeal nerve localization using a microlaryngeal electrode" (Otolaryngology—Head and Neck Surgery, Vol. 87, p. 330 ff.). However, because of technical difficulties and/or traumatizing derivation procedures, none of these methods was able to come into general use until now. The last method mentioned additionally has the disadvantage that only individual motor units are capable of derivation; the method therefore provides no information about the integrity of the nerve as a whole. Derivation by means of needle or hook electrodes, whatever type they may be, cannot reliably solve the problem of intraoperative monitoring. No continuous monitoring process exists.

J. Lee Rea, finally, in his essay "Postcricoid Surface Laryngeal Electrode" (Ear, Nose and Throat Journal, Vol. 71, No. 6, p. 267 ff.), describes the atraumatic derivation of the NLR by means of an element provided with surface electrodes, which is intended to be inserted into the glottis. However, the device described here is practically useless for its intended purpose, because its use can result in damage to the surrounding tissue. Furthermore, the device cannot be placed in the intended location with sufficient certainty, and dislocation during its use is not definitely precluded.

Dislocation of the electrodes and the inaccuracy of the derivation in case of only small movements of the endotracheal tube are the main problems of a derivation system which was described by Andrew Goldstone (EP-0438863 A1). Here, two wires are affixed on the tube exactly parallel to the tube axis, which are intended to detect electrical activity of the vocal cords. However, reliable derivation is not possible because if the tube is moved or turned only slightly, contact with the vocal cords can be lost. The different status of opening of the vocal cords can also cause a problem with derivation. The contact pressure which is changed when this occurs can result in amplitude changes of the signal, while the signal derivation is maintained. Recognition of the threat of lesion of the NLR and of the NLS will therefore fundamentally not take place with this device.

Continuous monitoring of the NLS and the NLR is not practicable with this device. Since a tube with a maximum thickness is always required in order to produce contact with the vocal cords, the risk of injury to the vocal cords increases dramatically, since the respiration tube with the surface wires running longitudinally on it must be forced through the vocal cords. It is possible that the vocal cords could be cut as a result. The device described by Goldstone can therefore not be used for the intended purpose.

The present invention is based on the task of creating a double-balloon endotracheal tube of the type stated initially, which represents a sufficiently sensitive detection and monitoring system which can be reliably positioned, and which, when using suitable evaluation devices, makes it possible to detect the course of the motor laryngeal nerves (NLR and NLS) in the tissue and to continuously monitor their function during the operation, in such a way that even slight and reversible lesions, which include impairment of only a few axons of the nerves, are detected, in order to indicate even the threat of injury, with continuous monitoring outside the OP field being possible, thereby for the first time not impairing the technical procedure of the operation.

In accordance with the present invention, this task is accomplished in that electrical and/or electromagnetic sensors are arranged on the surface of the top balloon. These sensors detect the electrical or electromagnetic activity of the tracheal muscles as the result of spontaneous activity or as the result of electrical stimulation of the laryngeal nerves. They therefore particularly show a change in the physical state of the vocal cords which rest against them which occurs as a reaction to electrical stimulation of the NLR and/or the NLS. The present invention therefore takes advantage of the recognition that if electrical stimulation of the NLR is continued, the physical state of the vocal cords already changes with such a slight mechanical impairment of the NLR, at which movement changes of the vocal cords which are evident by derivation do not yet occur. This has the result that compared with the known methods, which are based on derivation of movements of the vocal cords, a clearly lower mechanical impairment of the NLR can already be detected when using the endotracheal tube according to the invention. The special significance of the endotracheal tube according to the invention can be seen in that positioning of the stimulation electrodes and the sensors takes place during routine intubation of the patient and is concluded at the same time, and therefore no additional manipulation steps are required. Furthermore, the device as a whole is atraumatic for the patient.

The entire apparatus therefore lies outside the OP field and allows atraumatic monitoring of the NLR from before the first incision to the end of anesthesia.

It is true that a single-balloon tube, the electrodes of which are supposed to be able to be connected to an electrocardiograph or a defibrillator, is known (DE-GM 8915538), but this does not show any connection to the problem which the present invention has set itself the task of solving.

In a particularly preferred further development of the endotracheal tube according to the invention, the sensors arranged on the top balloon are structured as electrically conductive, particularly ribbon-like strip electrodes. Using these electrodes, it is possible to determine a change in the electrical potential of the vocal cords which rest against the strip electrodes. In this case, the physical size of the vocal cords which is being derived is therefore their electrical potential. Within the scope of the present invention, however, linear electrodes, for example, can also be used. It is practical if two electrodes are provided. However, for individual applications a different number of electrodes or different types of electromagnetic sensors can also be used to advantage.

In a further development of the endotracheal tube according to the invention, the electrodes on the top balloon are structured as a combination of stimulation/derivation electrodes, or additional stimulation electrodes are affixed. Also, a different type of electromagnetic stimulators is possible. This arrangement has the result that the sensor branches of the NLS can be stimulated via the mucosa of the trachea, for the first time, and are switched to the motor branch of the NLS via the known reflex arc *) in the vagal nucleus. The reflex arc signal ("H-Wave") reaches the m. cricothyroideus with a latency of approximately 5 ms. The sum action potential can then be derived via the sensors on the top balloon. The integrity of the entire NLS (including sensor and motor fibers) can therefore be monitored continuously during the operation (without touching the OP field), for the first time. This type of NLS stimulation, taking advantage of the reflex arc, is of particular significance, since this makes continuous monitoring of the NLS without touching the OP field, possible for the first time.

*) W. F. Thumfart "Electromyography of the larynx and related technics", Acta Oto Rhino Laryngologica Belgica 1986, 40:2, p. 358 ff.

In a further development of the endotracheal tube according to the invention which goes beyond this, stimulation electrodes for transtracheal stimulation of the NLR are arranged on the bottom balloon, a known stimulation technique which was suggested by J. A. Sercarz et al. in "Fabrication of a custom electrode endotracheal tube" (Laryngoscope 1991, 101; p. 1024–1025). The transtracheal stimulation of the NLR which becomes possible by the double-balloon endotracheal tube which was developed further in this way, in combination with the highly sensitive derivation described above, permits continuous intraoperative monitoring, for the first time, without the surgeon having to concern himself/herself with it in any way. It is practical, when using the tube according to the invention, if the NLR is first traced in the operating field using a bipolar electrode and subsequently a switch is made to transtracheal stimulation, so that the surgeon has both hands free from then on. The operation can therefore take place with continuous monitoring of nerve function, for the first time, without the operating procedure having to be changed.

For another area of application (measurement of the depth of anesthesia, i.e. the depth of relaxation in other operations), the endotracheal tube according to the invention is combined with the known hydraulic pressure measurement via the top balloon. This allows simultaneous detection of the mechanical activity in the glottis. This serves for precise follow-up control of the depth of anesthesia, i.e. the depth of relaxation of the patient, evident by the loss of motor activity (muscular paralysis) and maintenance of an electrical, i.e. electromagnetic residual activity of the muscles. The advantage as compared with the tests of depth of relaxation usually used until now, by means of stimulation of the hand nerves and observation of the resulting contraction of the hand muscles, is an exact and reproducible muscle strength measurement in addition to the EMG signal and therefore better control of the anesthesia, i.e. the depth of relaxation, by means of the endotracheal tube according to the invention. Vocal cord mobility is known to be dependent on the depth of relaxation of the patient (see the essay by J. O. Dich-Nielsen "Flexible fiberoptic bronchoscopy via the laryngeal mask"; (Acta Anaesthesiologica scandinavica 1991, 37; p. 17 ff.).

Figure 1:
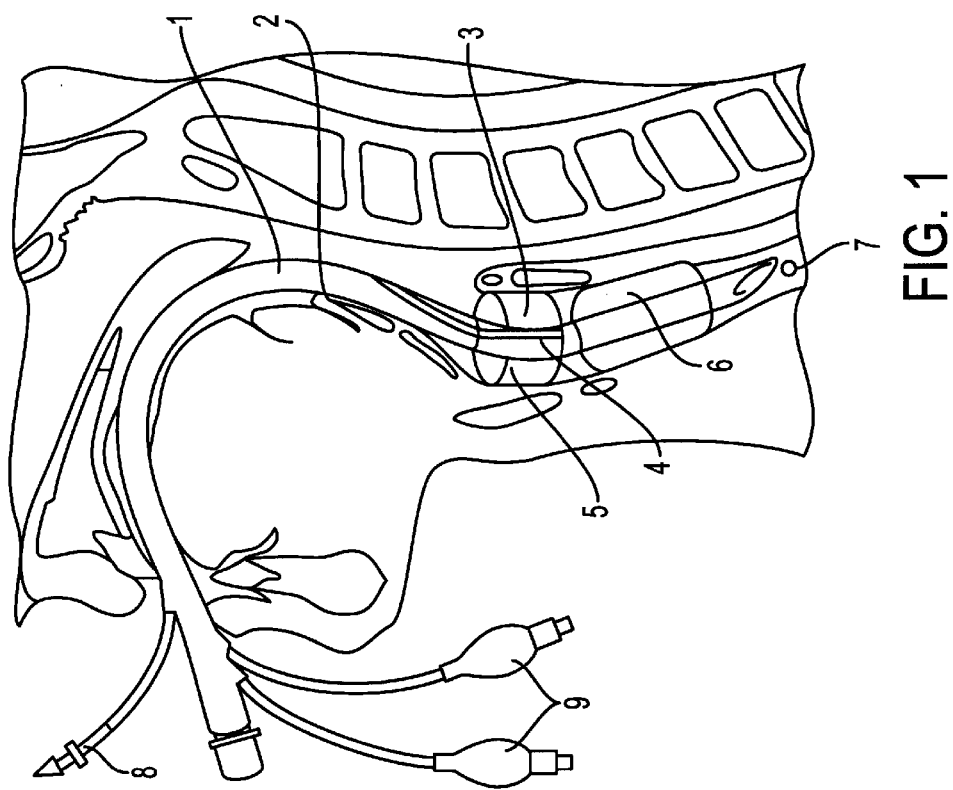
Figure 7:
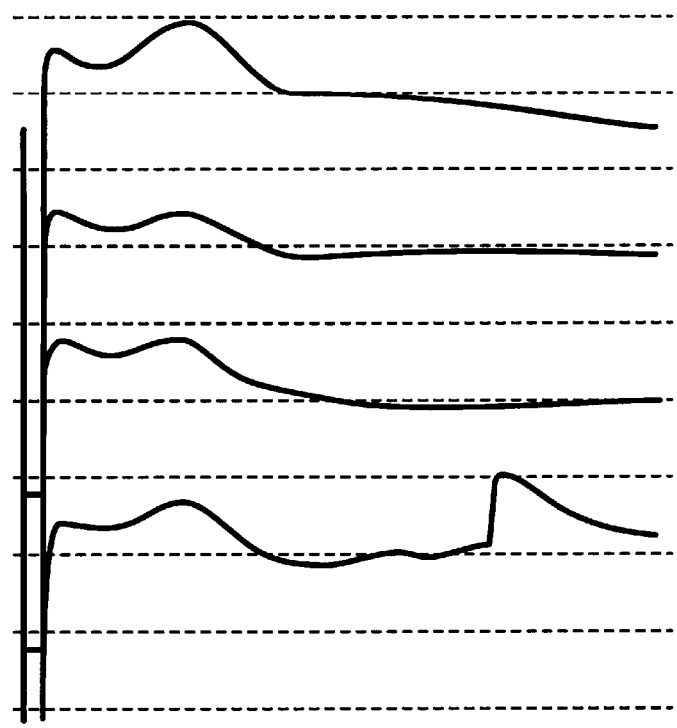
Figure 8:
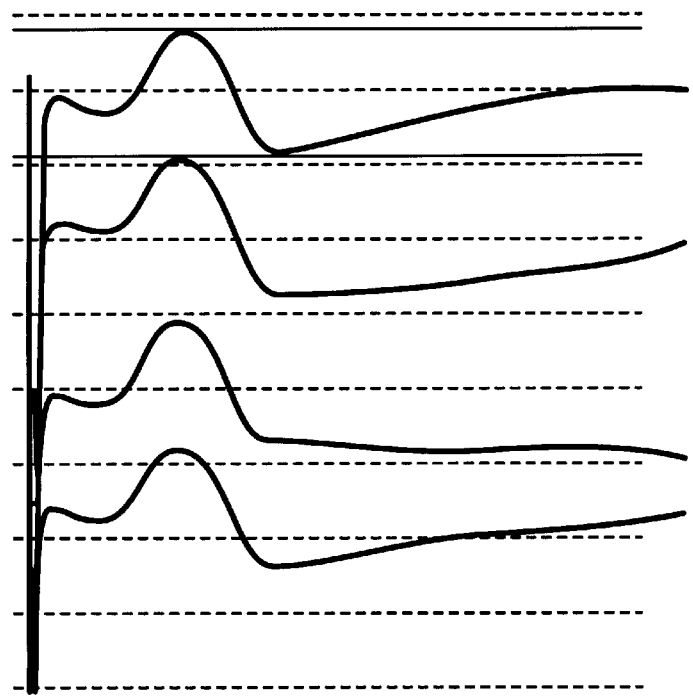
Figure 9:
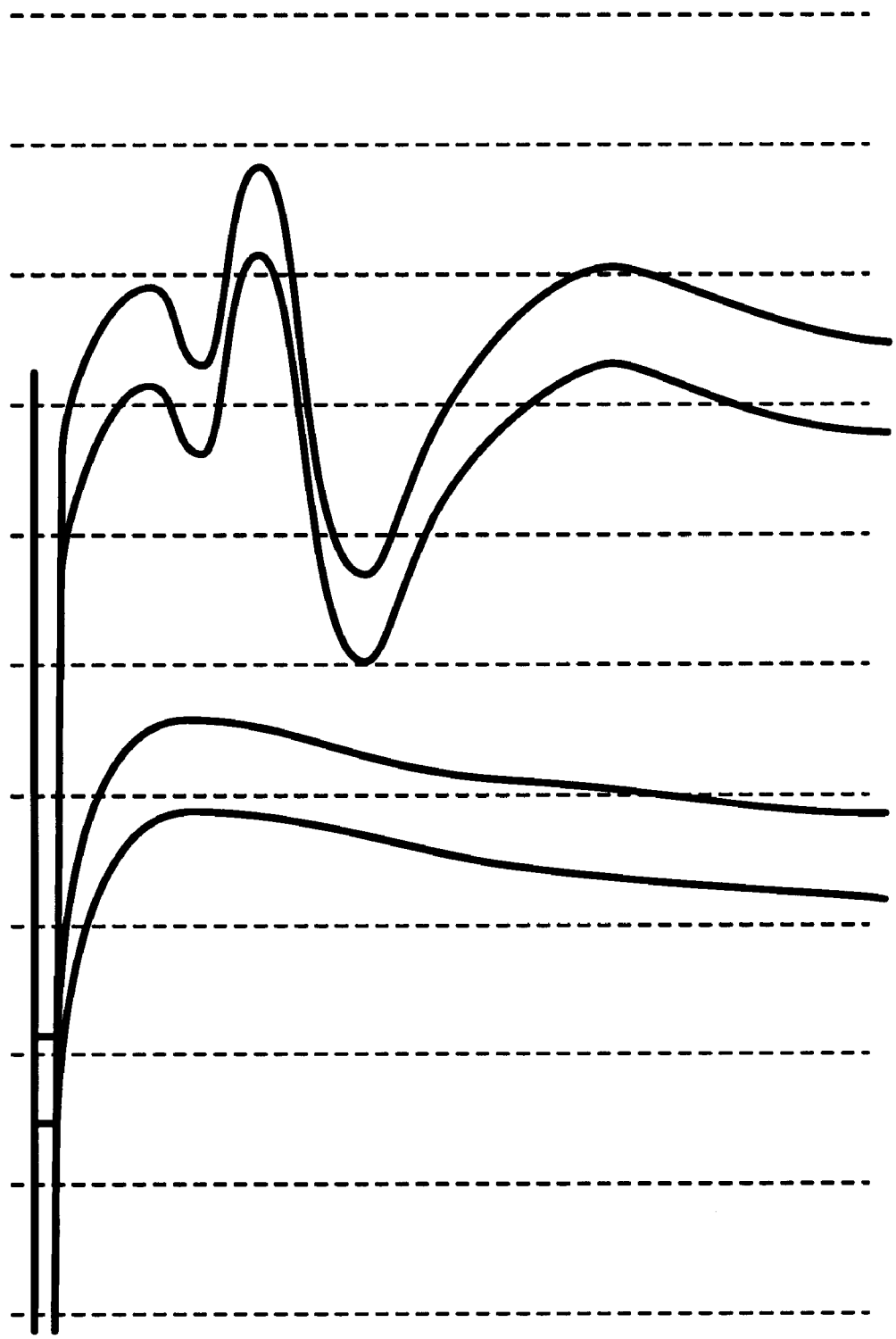
Figure 10:
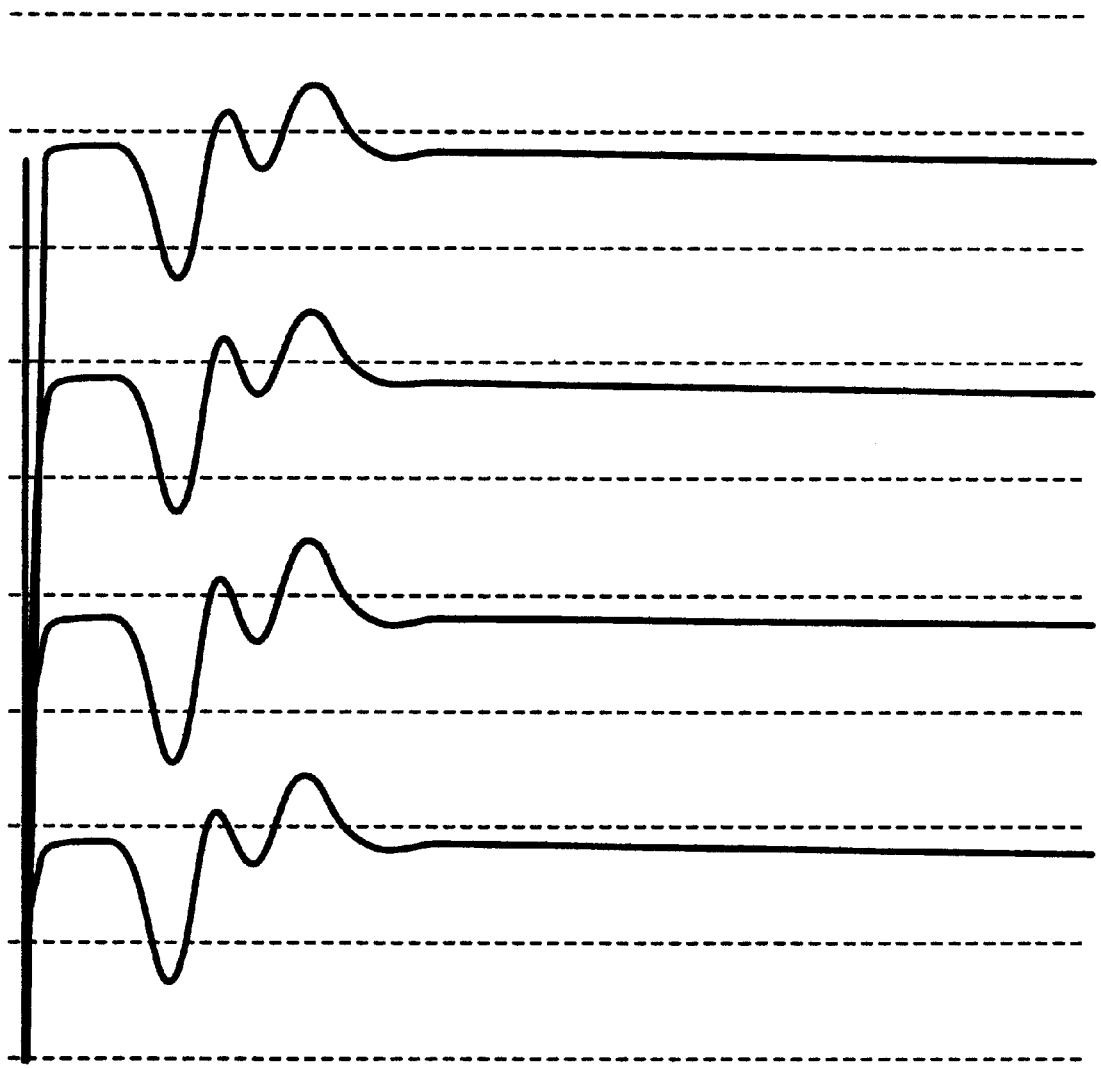

The invention will be explained in greater detail below, with reference to the drawing. This shows FIG. 1 a sagittal cross-section through a preferred exemplary embodiment of the endotracheal tube according to the invention, placed in the trachea;

FIG. 2 a frontal cross-section through the endotracheal tube according to FIG. 1, placed in the trachea, FIG. 3 to 8 different typical derived voltage progressions with the NLR unimpaired and mechanically impaired in different ways, FIG. 9 a typical voltage progression after transtracheal stimulation via a stimulation electrode on the bottom balloon without and with traumatic injury to the NLR, and FIG. 10 a typical voltage progression after stimulation of the NLS without traumatic injury.

The endotracheal tube according to FIG. 1 and 2 comprises a tube segment 1. Two balloons 3 and 6, which can be expanded independent of one another, by means of the two pump mechanisms 9, via corresponding connecting hoses, are arranged adjacent to the bottom end of the tube.

To this extent, the endotracheal tube shown in FIG. 1 corresponds to the state of the art available in commerce, so that no further explanations are required.

Two electrically conductive strip electrodes 4 are arranged on the surface of the top balloon 3, but only the one facing the observer is visible in FIG. 1, because of their relative position. An electrically conductive derivation cable is connected to each of the two strip electrodes 4, extending along the tube, fixed in place on its wall, to the bottom end. Connector plugs 8, to be connected to evaluation electronics, are provided at the ends of the two derivation cables.

FIG. 1 and 2 illustrate the placement of the endotracheal tube according to the invention in such a manner that the top balloon 3 comes to rest in the glottis. The musculus vocalis and the musculus thyroarytaenoideus 5 are indicated in FIG. 2; FIG. 1 shows the epiglottis. The trachea is indicated with 7 in each instance. The bottom balloon 6 forms a seal against it; at the same time, it reliably and definitely assures that the correct position of the top balloon 3 is maintained, even during operations which take a long time. It is clearly evident in FIG. 2 that the surface derivation electrodes 4 which are arranged on the top balloon 3 rest intimately against the vocal cords.

The derived voltages shown in FIG. 3 to 8 were recorded during experiments which were conducted in piglets, using the endotracheal tube according to FIG. 1 and 2. In these experiments, the following method of procedure was followed: Modified conventional atraumatic bipolar clamp electrodes were used as stimulation electrodes. The distance between electrodes was 1 cm. A monopolar wire electrode with a large-surface counter-electrode was used as the ground electrode. Nerve stimulation took place by means of a constant current stimulator at 10–20 mA.

The endotracheal tube (with balloons 3 and 6 completely deflated) was introduced into the trachea, specifically to such an extent that the bottom balloon 6 definitely lay below the glottis. Subsequently, the bottom balloon 6 was slightly pumped up (blocked). Then the endotracheal tube was retracted until the partially blocked bottom balloon caught in the subglottis. In this position of the tube, both the bottom balloon 6 and the top balloon 3 were expanded, so that the bottom balloon 6 sealed off the tube segment 1 relative to the trachea, and the strip electrodes 4 arranged on the top balloon 3 were in direct contact with the vocal cords.

The sum potentials of the vocal cord muscles shown in FIG. 3 to 8 (the organ controlled by the NLR) were derived via a standard EMG device ("Dantec Cantata"). A band-pass filter 20 Hz to 2 kHz was used in this connection. The amplification was 1 mV/raster. The derivation took place as a monopolar ipsilateral derivation on the vocal cord. The derived potentials were exactly reproducible in their shape and reached a signal intensity of 2.2 to 3.0 mV.

Figure 3:
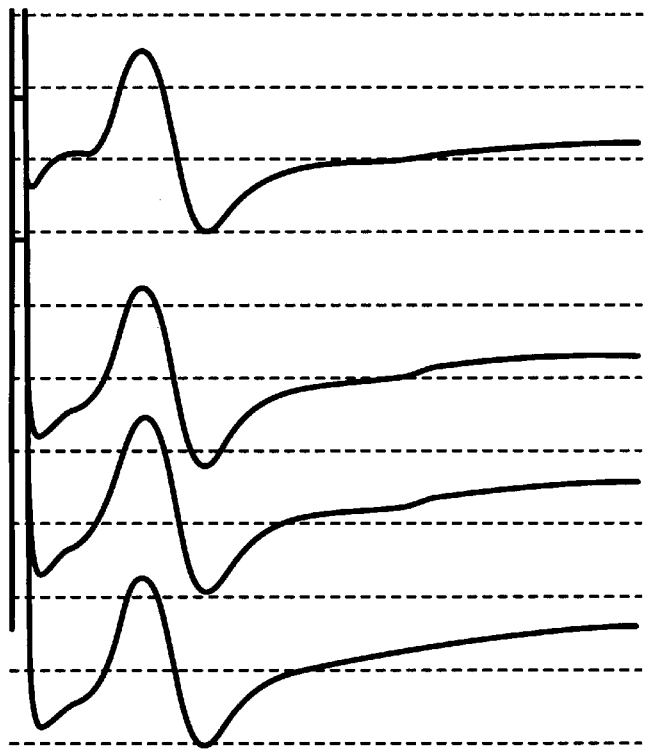
Figure 4:
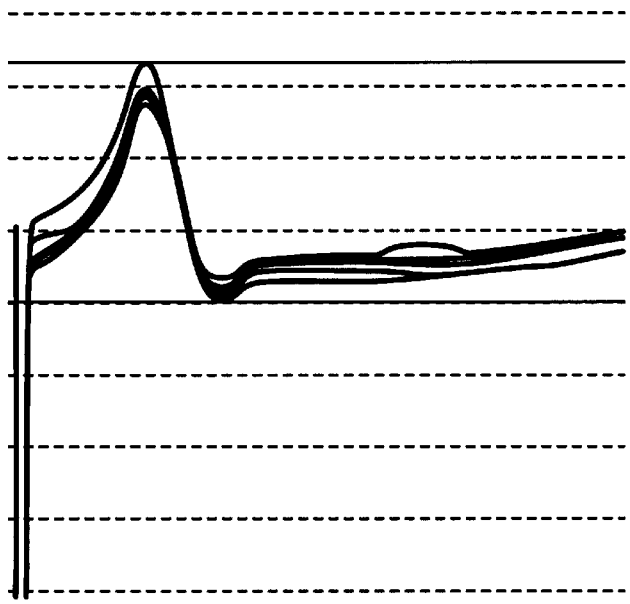

FIG. 3 shows four measurements, independent of one another, at time intervals of 0.5 to 4 min, which form a typical derivation after stimulation, with 14.3 mA, on peripheral nerves. Shown on the abscissa is the time progression (2 msec per raster). Shown on the ordinate is the derived voltage of the sum-action potential (1 mV per raster). FIG. 3 illustrates the good reproducibility of the derived potentials. To illustrate the reproducibility, four other derivations, independent of one another, were projected above one another in FIG. 4. The monomorphous signal progression is clearly evident in this manner. As in FIG. 3, in FIG. 4 the time progression is shown on the abscissa (2 msec per raster), and the derived voltage of the sum-action potential (1 mV per raster) is shown on the ordinate.

Figure 5:
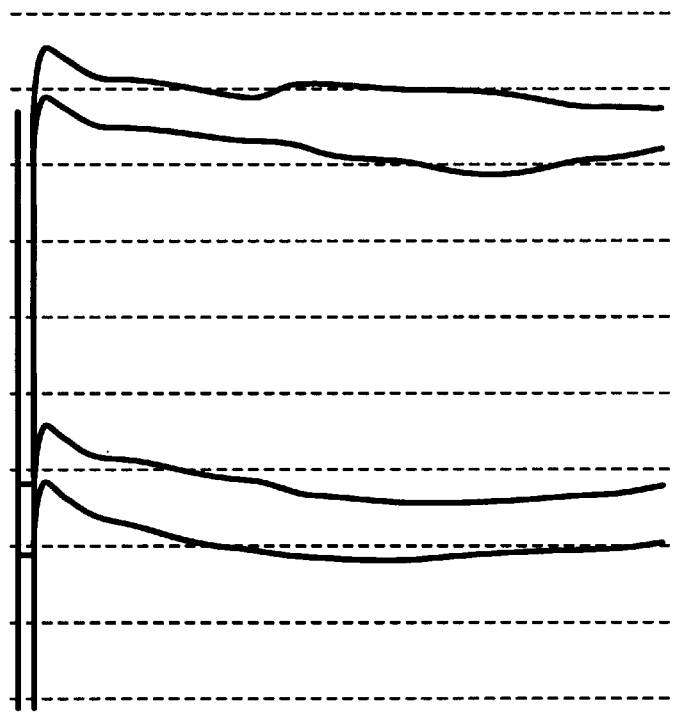

FIG. 5 shows the derived sum-action potential under the same conditions, after the corresponding NLR was compressed with tweezers. It is evident that this form of mechanical impairment of the NLR results in a complete loss of action potentials.

Figure 6:
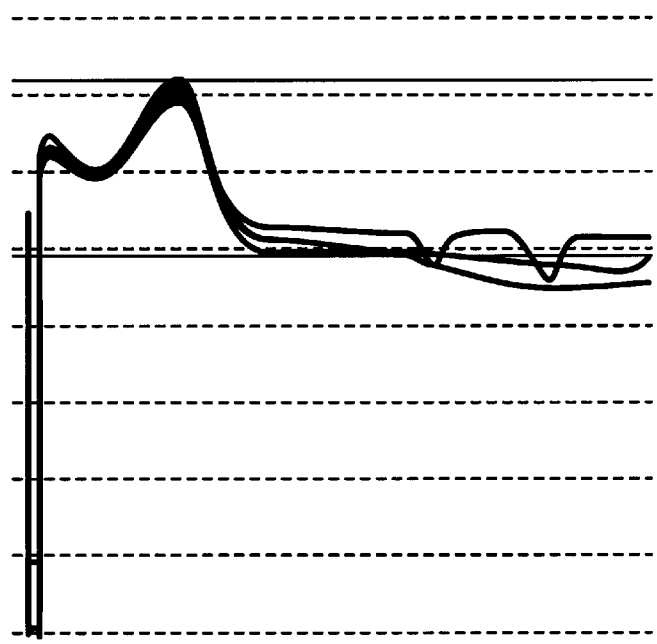

FIG. 6 shows the derived sum-action potentials after the tweezers were opened again and therefore decompression of the NLR occurred. It is evident that decompression of the NLR results in almost complete restoration of the nerve conductivity. The nerve conduction disturbance documented in FIG. 5 was therefore almost completely reversible. The slight broadening and lowering of the action potential, however, shows slight damage to the nerve which took place as the result of the severe compression.

The progressions of the sum-action potentials shown in FIG. 7 and 8, for two comparatively slight traumas to the nerve, are of particular importance. FIG. 7 shows the sum-action potentials in the case of very slight compression of the NLR, otherwise under the same conditions as in FIG. 3 to 6. It is evident that this lesser compression (as compared to the conditions underlying FIG. 5) results in partial loss of the action potential. This documents that even a relatively slight compression of the nerve, which does not leave any kind of permanent damage, can be detected using the tube according to the invention.

The same holds true for traction on the nerve, the effects of which are illustrated in FIG. 8. Even slight traction on the nerve results in clearly evident coarsening of the signal progression, shown by a comparison with FIG. 3, which reproduces the signal progression with an unimpaired NLR.

FIG. 9 illustrates the signal which results from transtracheal stimulation of the NLR by means of the stimulation electrodes provided on the lower balloon, and which permits excellent evaluation. With the exception of this stimulation electrode, the tube used was identical to the one explained above. And the test conditions also agreed with the ones described above. The two top curves reproduce typical voltage progressions without damage to the NLR; the two bottom curves were recorded for traumatic damage to the NLR. This further development of the endotracheal tube according to the invention now allows continuous intraoperative monitoring of the NLR, for the first time, without influencing the operative procedure, by means of stimulation and derivation outside of the OP field.

FIG. 10 illustrates the excellently reproducible and assessable sum-action potential which can be recorded as the reaction to stimulation of the NLS, using the tube according to the invention. In this way, it was possible to perform an intraoperative EMG derivation of the musculus cricothyroideus (organ controlled by the NLS) outside of the OP field, for the first time.

In a further development of the endotracheal tube according to the invention, stimulation of the NLS takes place outside the OP field by means of additional stimulation electrodes on the top balloon, which can also be identical with the derivation sensors. For this purpose, a known neurophysiological reflex arc can be used, which makes it possible to continuously monitor the entire NLS, including its sensor fibers, over its entire course.

What is claimed is:

1. An endotracheal tube comprising a tube segment and a pair of expandable balloons, one of said balloons being an upper balloon and the other of said balloons being a lower balloon, said balloons being spaced from each other along the longitudinal axis of said tube segment, said balloons being independeetly expandable, said upper balloon having atraumatic sensors arranged on its surface to contact the inner surface of the vocal cords and said lower balloon having at least one electrode on its surface, said electrode being positioned to stimulate the recurrent laryngeal nerve at the surface of the trachea.

2. The endotracheal tube according to claim 1 wherein said sensors are structured as an electrically conductive surface coating on said top balloon.

3. The endotracheal tube according to claim 1 wherein said sensors on said top balloon are strctured as a combination of one or more stimulationl/derivation electrodes.

4. The endotracheal tube according to claim 1 wherein said at least one electrode on said lower balloon provides transtraheal or transbronchial stimulation of the recurrent laryngeal nerve.

5. The endotracheal tbe according to claim 1 wherein said sensors on said top balloon are electrical.

6. The endotracheal tube according to claim 1 wherein said sensors on said top balloon are electromagnetic.

* * * * *